US008016801B2

(12) United States Patent
Clarke

(10) Patent No.: US 8,016,801 B2
(45) Date of Patent: Sep. 13, 2011

(54) EXFOLIATING DEVICE

(76) Inventor: Jennifer Clarke, Santa Rosa, CA (US)

( * ) Notice: Subject to any disclaimer, the term of this patent is extended or adjusted under 35 U.S.C. 154(b) by 660 days.

(21) Appl. No.: 12/098,698

(22) Filed: Apr. 7, 2008

(65) Prior Publication Data
US 2009/0254055 A1  Oct. 8, 2009

(51) Int. Cl.
*A61M 35/00* (2006.01)
*A45D 33/28* (2006.01)
(52) U.S. Cl. ............................ 604/310; 132/297
(58) Field of Classification Search ............... 401/129; 604/309–312, 1–3; 132/297
See application file for complete search history.

(56) References Cited

U.S. PATENT DOCUMENTS

| | | | | |
|---|---|---|---|---|
| 2,094,006 A | * | 9/1937 | O'Moore-Farrell | 132/318 |
| 2,129,051 A | * | 9/1938 | Eastley | 401/19 |
| 2,143,061 A | * | 1/1939 | Eastley | 132/318 |
| 2,177,651 A | * | 10/1939 | Harris | 401/19 |
| 2,196,127 A | * | 4/1940 | Stogran | 401/19 |
| 2,219,754 A | * | 10/1940 | Skold | 132/318 |
| 2,236,240 A | * | 3/1941 | Lowen | 401/99 |
| 2,264,482 A | * | 12/1941 | Ridner, Sr. et al. | 401/11 |
| 2,458,063 A | * | 1/1949 | Dulberg | 132/314 |
| 2,545,091 A | * | 3/1951 | Livermore | 15/184 |
| 2,552,714 A | * | 5/1951 | Gardiner | 401/18 |
| 2,590,329 A | * | 3/1952 | Kromray | 401/124 |
| 2,598,493 A | * | 5/1952 | Bogin et al. | 401/209 |
| 2,710,614 A | * | 6/1955 | Dulberg | 132/318 |
| 2,726,760 A | * | 12/1955 | Dulberg | 401/63 |
| 2,751,914 A | * | 6/1956 | Katz | 132/316 |
| 2,763,882 A | * | 9/1956 | Planka | 401/209 |
| 2,902,041 A | * | 9/1959 | Bau | 132/318 |
| 3,171,416 A | * | 3/1965 | Pimentel | 132/297 |
| 3,359,992 A | * | 12/1967 | Cishek et al. | 401/101 |
| 3,690,777 A | * | 9/1972 | Costa | 401/17 |
| 3,757,782 A | * | 9/1973 | Aiken | 604/3 |
| 5,002,415 A | * | 3/1991 | Gueret | 401/126 |
| 5,056,179 A | * | 10/1991 | Capponi | 15/105 |
| 5,178,478 A | * | 1/1993 | Ryder | 401/195 |
| 5,180,084 A | * | 1/1993 | Favre | 222/192 |
| 5,316,398 A | * | 5/1994 | Chandaria et al. | 401/18 |
| 5,450,865 A | * | 9/1995 | Park | 132/218 |
| 5,833,962 A | * | 11/1998 | Chen | 401/59 |
| 5,881,742 A | * | 3/1999 | Hunsberger | 132/297 |
| 5,906,214 A | * | 5/1999 | Gueret | 132/314 |
| 5,941,254 A | * | 8/1999 | Heler | 132/297 |
| 5,983,905 A | * | 11/1999 | Patching | 132/318 |
| 6,241,408 B1 | * | 6/2001 | Lang | 401/17 |
| 6,405,737 B1 | * | 6/2002 | Sheffler et al. | 132/318 |
| 6,450,179 B2 | * | 9/2002 | Bengis | 132/297 |
| 6,612,764 B2 | * | 9/2003 | Dumler et al. | 401/18 |
| 6,682,242 B1 | * | 1/2004 | Montoli | 401/18 |
| 6,688,796 B1 | * | 2/2004 | Liu | 401/277 |
| 6,789,971 B2 | * | 9/2004 | Tsaur | 401/133 |
| 7,287,923 B1 | * | 10/2007 | Chen | 401/18 |
| 2003/0060746 A1 | * | 3/2003 | Mark | 604/3 |
| 2004/0078910 A1 | * | 4/2004 | Grote | 15/106 |
| 2004/0187885 A1 | * | 9/2004 | Strong et al. | 132/301 |
| 2006/0093425 A1 | * | 5/2006 | Gueret | 401/129 |
| 2006/0188318 A1 | * | 8/2006 | Gueret | 401/129 |
| 2006/0207627 A1 | * | 9/2006 | Thorpe et al. | 132/320 |
| 2007/0151061 A1 | * | 7/2007 | Mink et al. | 15/160 |
| 2009/0097899 A1 | * | 4/2009 | Carroll | 401/109 |

\* cited by examiner

*Primary Examiner* — Jacqueline F Stephens
*Assistant Examiner* — Paula Craig
(74) *Attorney, Agent, or Firm* — Bay Area Technology Law Group PC

(57) ABSTRACT

A unitary device for exfoliating and applying emollient balm to lips of a user. The device is in the form of a hollow body having a longitudinal axis and extending from a first end thereof, a brush having bristles emanating from a support and an applicator extending from a second end of the hollow body together with the supply of emollient balm.

6 Claims, 1 Drawing Sheet

EXFOLIATING DEVICE

TECHNICAL FIELD

The present invention is directed to exfoliating and conditioning the lips of a user through the use of a unitary device housing both bristles for exfoliating the lips of a user's skin and an emollient balm for soothing and revitalizing the exfoliated skin.

BACKGROUND OF THE INVENTION

Lips are a facial feature which are oftentimes ignored both in terms of their aesthetic appeal and one's need to protect them against whether and other environmental irritants. This is particularly true because lips are more vulnerable to the environment than any other part of the face as they do not contain oil glands.

It is further known that if lips are exfoliated through abrasion, old dry skin can be removed and replenished while lips take on a puffy and rather perky appearance enhancing their aesthetic appeal. However, when exfoliated, lips can further be irritated which only further aggravates those environmental impacts discussed above.

It is critical that anyone exfoliating lips through abrasion also employ an emollient balm. It is thus important that there be a unitary device that couples the abrading means with the emollient balm source to ensure that the exfoliating and subsequent emollient treatments be always carried out in tandem.

SUMMARY OF THE INVENTION

A unitary device for exfoliating and applying emollient balm to lips of a user. The device is in the form of a hollow body having a longitudinal axis and extending from a first end thereof, a brush having bristles emanating from a support and an applicator extending from a second end of the hollow body together with the supply of emollient balm.

DETAILED DESCRIPTION OF THE INVENTION

As noted previously, the present invention involves a unitary device for providing exfoliating means with an emollient balm to ensure that both expedients are available to a user in tandem. In this regard, reference is made to FIG. 1 showing a preferred embodiment of the present invention.

Figure 1:
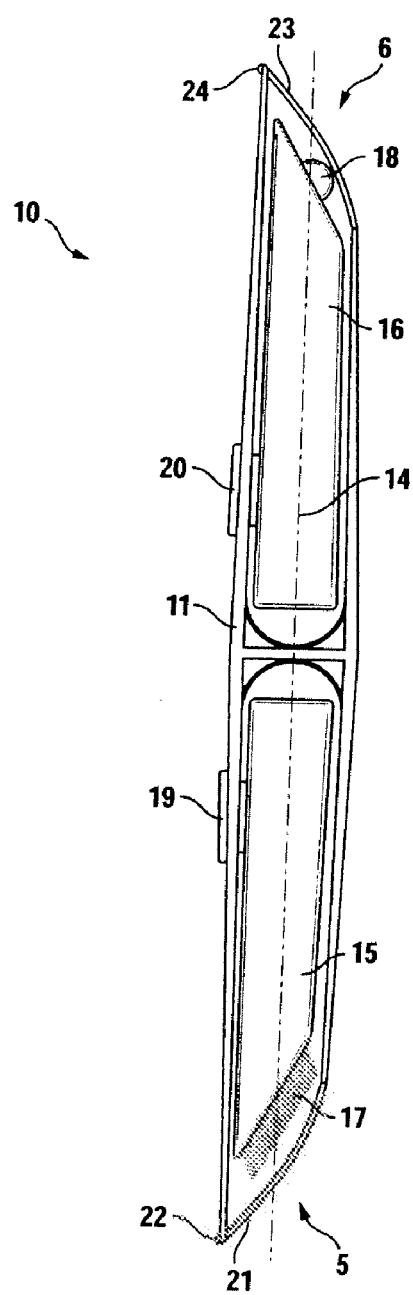
FIG. 1 is a cut away perspective view of a preferred embodiment of the present invention.

Turning to FIG. 1, unitary device 10 is depicted for exfoliating and for applying an emollient balm to lips of a user. The device comprises hollow body 11 extending from first end 5 to second end 6 thereof. A brush having bristles 17 emanates from support 15 which, as noted in FIG. 1, is fully enclosed within hollow body 11 when not in use. Similarly, proximate second end 6 is an applicator 16 containing a supply of emollient balm therein.

Figure 2:
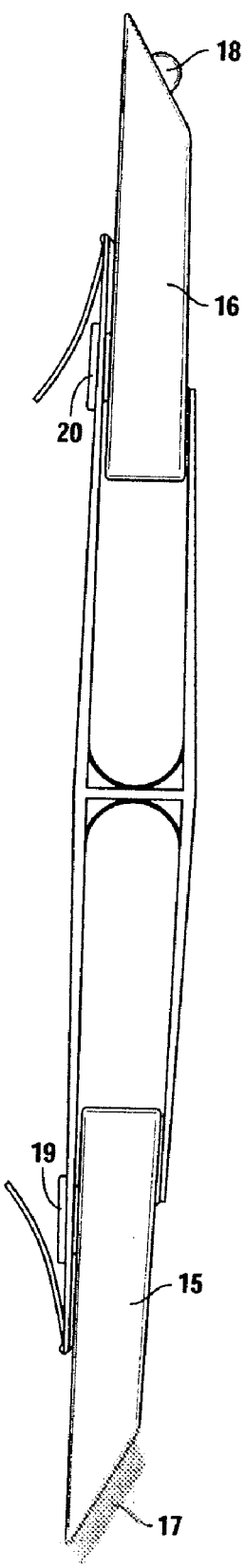
FIG. 2 is a perspective of the embodiment of FIG. 1 in a second orientation.

In its closed orientation as depicted in FIG. 1, first and second ends 5 and 6 are closed by virtue of doors or flaps 21 and 23, respectively. When deploying the present invention, sliders 19 and 20 extend outwardly along longitudinal axis 14 causing flaps or doors 21 and 23 to move about hinges 22 and 24 while extending bristle support 15 and emollient balm applicator 16 from hollow body 11 as shown in FIG. 2.

As a preferred embodiment of the present invention, bristle 17 extends from support 15 terminating on a plane at an angle from approximately 20 degrees to 75 degrees from said the longitudinal axis. This provides a beveled surface most appropriate for running the bristles along a user's lips for exfoliating. Most users would find this most pleasing in that providing a beveled relationship between longitudinal axis 14 and the bristle surface connotes an angle which most lipstick manufacturers employ in fabricating their products.

The emollient balm housed within applicator 16 can be of any suitable configuration for applying a semi viscous liquid to one's lips. It is suggested, as a preferred embodiment, that roller ball 18 can be used for this purpose. It should be quite apparent that the device of the present invention can be employed by actuating emollient balm supply 16 independent of bristle support 15. As such, one can employ the present invention to apply an emollient balm if one's lips are chapped or otherwise needing a soothing medicant without subjecting the user's lips to exfoliating abrasion.

Any commercially available balms can be used in practicing the present invention. All generally contain soothing ingredients such as lanolin, shea butter and cocoa butter. Medicated balms, such as Blistex®, containing 5% phenol are also useful.

What is claimed is:

1. A unitary device for exfoliating and for applying an emollient balm to lips of a user, said device comprising a hollow body having a longitudinal axis and extending from a first end of the hollow body, a brush having bristles emanating from a support and an applicator extending from a second end of said hollow body together with a supply of emollient balm, wherein a reservoir of said emollient balm is housed within a substantially hollow cylinder used to supply said applicator; and said bristle support and hollow cylinder are oriented along said longitudinal axis and slidable between first and second orientations.

2. The unitary device of claim 1 wherein said brush comprises a plurality of bristles terminating on a plane at an angle from approximately 20 degrees to 75 degrees from said longitudinal axis.

3. The unitary device of claim 1 wherein in said first orientation, said bristles and said applicator are contained within said hollow body and in said second orientation, said bristles and applicator extend outwardly from said first and second ends thereof.

4. The unitary device of claim 1 wherein said bristles and applicator can be positioned at said first and second orientations independently of one another.

5. The unitary device of claim 1 further comprising closures hinged to said first and second ends of said hollow body to close said ends when said bristles and applicator are in said first orientations.

6. The unitary device of claim 1 wherein said applicator comprises a roller ball.

* * * * *